US008633330B2

(12) United States Patent
Merz, III et al.

(10) Patent No.: US 8,633,330 B2
(45) Date of Patent: Jan. 21, 2014

(54) PROCESS FOR PREPARING MONOALKYLTIN TRIHALIDES AND DIALKYLTIN DIHALIDES

(75) Inventors: George J. Merz, III, Mobile, AL (US); Michelle F. Walasavage, Orwigsburg, PA (US); Berth Jan Deelman, DW Kapelle (NL); Maarten D. K. Boele, GP Goes (NL); Andrew R. Goddard, Malvern, PA (US); William D. Honnick, Exton, PA (US)

(73) Assignee: PMC Organometallix, Inc., Mt. Laurel, NJ (US)

( * ) Notice: Subject to any disclaimer, the term of this patent is extended or adjusted under 35 U.S.C. 154(b) by 0 days.

(21) Appl. No.: 13/807,756

(22) PCT Filed: Jul. 1, 2011

(86) PCT No.: PCT/US2011/042730
§ 371 (c)(1),
(2), (4) Date: Jul. 12, 2013

(87) PCT Pub. No.: WO2012/003415
PCT Pub. Date: Jan. 5, 2012

(65) Prior Publication Data
US 2013/0281725 A1    Oct. 24, 2013

Related U.S. Application Data
(60) Provisional application No. 61/360,525, filed on Jul. 1, 2010.

(51) Int. Cl.
C07F 7/22    (2006.01)
(52) U.S. Cl.
USPC ............... 556/95; 556/87; 556/97; 556/104

(58) Field of Classification Search
USPC .................................. 556/87, 95, 97, 104
See application file for complete search history.

(56) References Cited

U.S. PATENT DOCUMENTS

| 2,962,522 | A | | 11/1960 | Rosenberg et al. | |
|---|---|---|---|---|---|
| 3,415,857 | A | | 12/1968 | Hoye | |
| 3,459,779 | A | | 8/1969 | Neumann | |
| 3,957,839 | A | * | 5/1976 | Sundermeyer et al. | 556/97 |
| 3,971,817 | A | * | 7/1976 | Jung et al. | 556/97 |
| 4,148,814 | A | * | 4/1979 | Reifenberg | 556/97 |
| 5,654,457 | A | * | 8/1997 | Bergfried et al. | 556/89 |
| 6,768,017 | B2 | * | 7/2004 | Thoonen et al. | 556/97 |
| 6,846,944 | B2 | * | 1/2005 | Schumacher et al. | 556/104 |
| 7,592,472 | B2 | * | 9/2009 | Boele et al. | 556/95 |
| 2004/0133022 | A1 | | 7/2004 | Schumacher et al. | |
| 2009/0131704 | A1 | | 5/2009 | Boele et al. | |

OTHER PUBLICATIONS

International Search Report and Written Opinion; International Application No. PCT/US2011/042730; International Filing Date: Jul. 1, 2011; 3 pages.

* cited by examiner

Primary Examiner — Porfirio Nazario Gonzalez
(74) Attorney, Agent, or Firm — Blank Rome LLP (57) ABSTRACT

The invention provides a process for producing monoalkyltin trihalide or a mixture of monoalkyltin trihalide and dialkyltin dihalide by: (a) contacting dialkyltin dihalide with an alkylation agent and, optionally, tin tetrahalide, to form a tetraalkyltin mixture comprising tetraalkyltin, trialkyltin halide, and dialkyltin dihalide; (b) reacting the tetraalkyltin mixture with tin tetrahalide to form a monoalkyltin trihalide mixture comprising monoalkyltin trihalide, dialkyltin dihalide and optionally triakyltin halide; (c) processing the monoalkyltin trihalide mixture to separately recover the monoalkyltin trihalide and a dialkyltin dihalide stream optionally containing trialkyltin halide; and (d) recycling at least a portion of the dialkyltin dihalide stream recovered in step (c) to the contacting step (a).

20 Claims, 4 Drawing Sheets

PROCESS FOR PREPARING MONOALKYLTIN TRIHALIDES AND DIALKYLTIN DIHALIDES

FIELD OF THE INVENTION

The invention relates to a process for the preparation of monoalkyltin trihalides or mixtures of monoalkyltin trihalides and dialkyltin dihalides.

BACKGROUND OF THE INVENTION

Monoalkyltin trihalides or mixtures of monoalkyltin trihalides and dialkyltin dihalides, such as monoalkyltin trichlorides of the formula $RSnCl_3$ or dialkyltin dichlorides of the formula $R_2SnCl_2$ (R being $C_nH_{2n+1}$ where $n \geq 1$, particularly methyl-, butyl- and octyltin trichloride), for example, are industrially important as intermediates for PVC stabilizers, glass coating chemicals, catalysts, etc.

Trialkyltin compounds are known to be toxic compounds. The toxicity of tin compounds may be linked to the presence of mono-, di- and tri-alkyltin compounds, particularly where toxicity increases with increased alkyl groups. Thus, toxicity increases from mono-, to di- to tri-alkyltin compounds. Therefore, it is desired to develop monoalkyltin compounds, with low levels of di- and tri-alkyltin compounds, in order to avoid or minimize toxicity issues.

Conventional methods of producing monoalkyltin trihalides suffer from a number of drawbacks, such as requiring expensive catalysts (e.g., precious metal catalysts) or high reaction temperatures, attaining low yields of monoalkyltin trihalides and/or high yields of by-products, such as trialkyltin compounds, or requiring multiple step processes, which produce monoalkyltin trihalide as a by-product instead of as the primary product.

SUMMARY OF THE INVENTION

The present invention provides a high yield, high purity monoalkyltin trihalide product and a process for producing the monoalkyltin trihalide and dialkyltin dihalide, such as monobutyltin trichloride and dibutyltin dichloride, respectively. The present invention provides a process that is capable of converting 60% to 99%, or nearly all, of the tin in tin tetrahalide into monoalkyltin trihalide in high yield and simultaneously a dialkyltin dihalide with less than 1 mole % trialkyltin halide. The high purity monoalkyltin compounds or mixtures of monoalkyltin trihalides and dialkyltin dihalides may be produced by using a process that reuses or recycles part or all of the co-produced dialkyltin dihalide as a raw material.

According to an embodiment of the present invention, a process for producing monoalkyltin trihalide and/or a mixture of monoalkyltin trihalide, dialkyltin dihalide and optionally trialkyltin halide comprises:

(a) contacting dialkyltin dihalide with an alkylation agent and, optionally, tin tetrahalide, to form a tetraalkyltin mixture comprising tetraalkyltin, trialkyltin halide, and dialkyltin dihalide, which may be depicted as:

where R is an alkyl group of the formula $C_nH_{2n+1}$, $n \geq 1$, and X is a halide;

(b) reacting the tetraalkyltin mixture with tin tetrahalide to form a monoalkyltin trihalide mixture comprising monoalkyltin trihalide, dialkyltin dihalide, and optionally trialkyltin halide, which may be depicted as:

where R is an alkyl group of the formula $C_nH_{2n+1}$, $n \geq 1$, and X is a halide;

(c) processing the monoalkyltin trihalide mixture to separately recover the monoalkyltin trihalide and a dialkyltin dihalide stream containing dialkyltin dihalide and optionally trialkyl halide; and

(d) recycling at least a portion of the dialkyltin dihalide stream recovered in step (c) to the contacting step (a).

According to another embodiment of the present invention, a process for producing monobutyltin trichloride and optionally a mixture of monobutyltin trichloride and dibutyltin dichloride comprises:

(a) contacting dibutyltin dichloride with an alkylation agent and, optionally, tin tetrachloride, to form a tetrabutyltin mixture comprising tetrabutyltin, tributyltin chloride, and dibutyltin dichloride, which may be depicted as:

(b) reacting the tetrabutyltin mixture with tin tetrachloride to form a monobutyltin trichloride mixture comprising monobutyl tin trichloride, dibutyltin dichloride, and optionally tributyltin chloride which may be depicted as:

(c) processing the monobutyltin trichloride mixture to separately recover the monobutyltin trichloride and a dibutyltin dichloride stream containing dibutyltin dichloride, and optionally tributyltin chloride; and (d) recycling at least a portion of the dibutyltin dichloride stream recovered in step (c) to the contacting step (a).

According to another embodiment of the present invention, a monoalkyltin trihalide is produced by:

(a) contacting dialkyltin dihalide with an alkylation agent and, optionally, tin tetrahalide, to form a tetraalkyltin mixture comprising tetraalkyltin, trialkyltin halide, and dialkyltin dihalide;

(b) reacting the tetraalkyltin mixture with tin tetrahalide to form a monoalkyltin trihalide mixture comprising monoalkyltin trihalide and dialkyltin dihalide;

(c) processing the monoalkyltin trihalide mixture to separately recover the monoalkyltin trihalide and the dialkyltin dihalide; and (d) recycling at least a portion of the dialkyltin dihalide recovered in step (c) to the contacting step (a).

BRIEF DESCRIPTION OF THE DRAWINGS

The present invention may be further understood with reference to the Figures in which.

DETAILED DESCRIPTION OF THE INVENTION

Aspects of the present invention include high purity monoalkyltin trihalide products and processes for producing the same. The high purity monoalkyltin compounds or mixtures of monoalkyltin trihalides and dialkyltin dihalides may be produced by using a process that reuses or recycles part or all of the co-produced dialkyltin dihalide as a raw material. In some embodiments, the stream that is recycled containing the dialkyltin dihalide may also optionally contain trialkyltin halide. Although, generally it is desired to keep the amount of trialkyltin halide at low levels in this stream (e.g., less than 5 mol % based on the total moles of tin in the dialkyltin dihalide stream), it is possible that this level be higher, for example 5 to 50 mol % trialkyltin halide.

As used herein, each species may be discussed interchangeably with respect to its chemical formula, chemical name, etc. For example, monoalkyltin trihalides may be used interchangeably with $RSnX_3$ where R is an alkyl group of the formula $C_nH_{2n+1}$, $n \geq 1$, and X is halogen atom. Table 1 provides a representative list.

TABLE 1

| | |
|---|---|
| monoalkyltin trihalides | $RSnX_3$ |
| dialkyltin dihalide | $R_2SnX_2$ |
| trialkyltin halide | $R_3SnX$ |
| tin tetrahalide | $SnX_4$ |
| tetraalkyltin | $R_4Sn$ |

Each compound described herein, unless designated otherwise, includes its different isomers and stereoisomers, including all single configurational isomers, single stereoisomers, and any combination thereof in any ratio. All values provided herein include up to and including the endpoints given.

Figure 1:
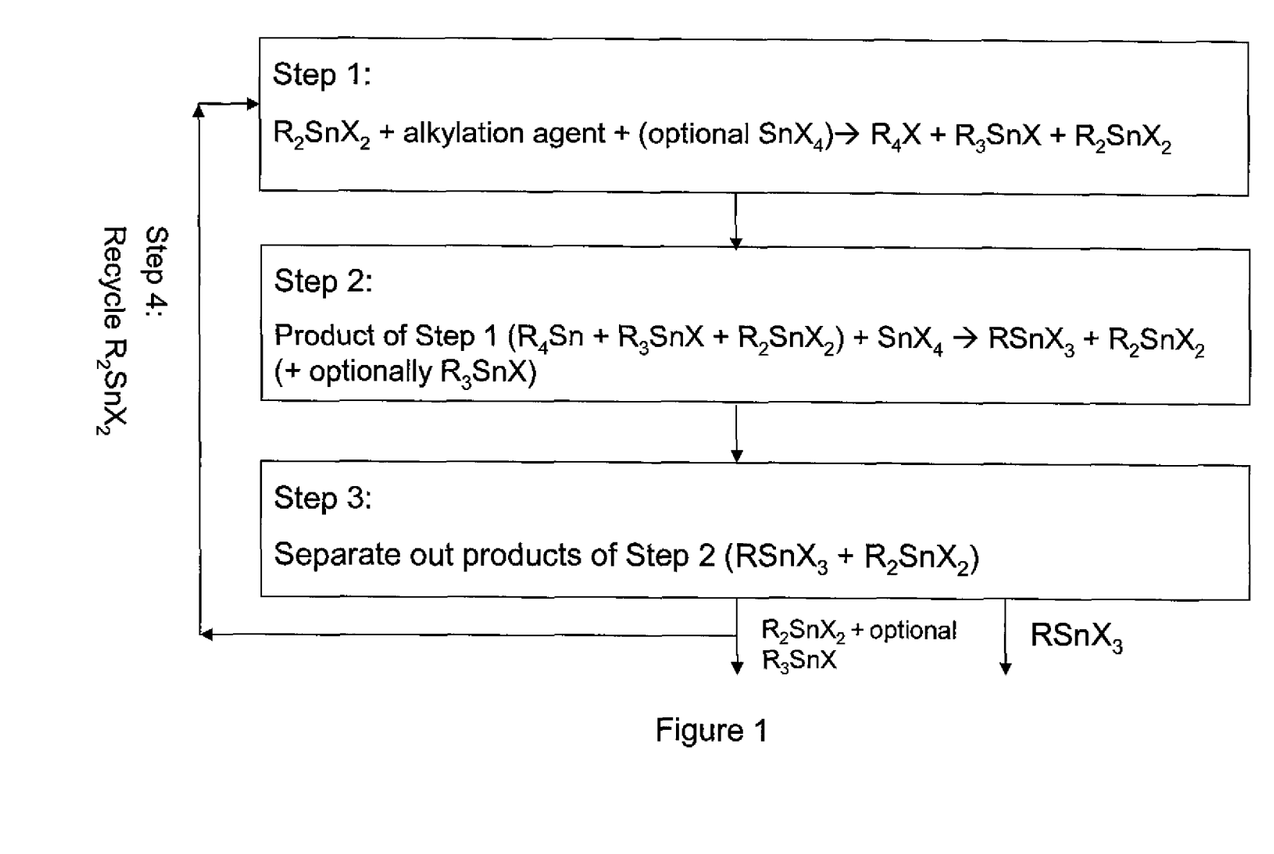
FIG. 1 depicts one embodiment of the present invention showing a four step cyclic process for producing a high yield and high purity monoalkyltin trihalide.

In an embodiment of the present invention and as depicted in FIG. 1, a process for producing monoalkyltin trihalide or mixtures of monoalkyltin trihalide and dialkyltin dihalide comprises:

(a) contacting dialkyltin dihalide with an alkylation agent and, optionally, tin tetrahalide, to form a tetraalkyltin mixture comprising tetraalkyltin, trialkyltin halide, and dialkyltin dihalide (step 1);

(b) reacting the tetraalkyltin mixture with tin tetrahalide to form a monoalkyltin trihalide mixture comprising monoalkyltin trihalide, dialkyltin dihalide and optionally trialkyltin halide (step 2);

(c) processing the monoalkyltin trihalide mixture to separately recover the monoalkyltin trihalide and a dialkyltin dihalide stream optionally containing trialkyltin halide (step 3); and (d) recycling at least a portion of the dialkyltin dihalide stream recovered in step (c) to the contacting step (a) (step 4).

It has been found that the cyclic process of recycling dialkyltin dihalides can be used to provide a high purity monoalkyltin trichloride with minimal amounts of the by-product, trialkyltin halide. In the cyclic process, a dialkyltin dihalide is first contacted with an alkylation agent as shown in step 1 of FIGS. 1 and 2.

For the dialkyltin dihalide of the formula $R_2SnX_2$, R is an alkyl group of the formula $C_nH_{2n+1}$ where $n \geq 1$ and X is a halide. R may be defined as an alkyl (linear or branched) or cycloalkyl having from 1 to 20 carbon atoms. According to one embodiment, R is selected from methyl, ethyl, n-propyl, iso-propyl, n-butyl, iso-butyl, n-pentyl, n-hexyl, n-heptyl, n-octyl, 2-ethylhexyl, iso-octyl, decyl, octadecyl, and eicosyl. More preferably R is a methyl, n-butyl, 2-ethylhexyl, n-octyl, or n-decyl group. In a preferred embodiment, R is n-butyl or n-octyl. The X gaup is a halide. The halide may be selected from the group consisting of fluoride (F), chloride (Cl), bromide (Br), iodide (I), and astatide (At), preferably chloride (Cl), bromide (Br), or iodide (I). According to a preferred embodiment, the halide is chloride. Any suitable dialkyltin dihalide may be used from any suitable source. According to the invention, the source of at least some if not all of the dialkyltin dihalide is as a recycled feed from the product stream.

The dialkyltin dihalide is contacted and reacted with an alkylation agent. The alkylation agent is used in a partial or complete alkylation reaction to transfer at least one alkyl group. Any suitable alkylation agent known to one skilled in the art may be selected, such as alkylaluminum compounds, alkylmagnesium compounds, dialkylmagnesium compounds, alkyllithium compounds, alkyl zinc compounds, etc. For example, the alkylation agent may be a Grignard reagent (e.g., an organomagnesium compound).

In one embodiment of the present invention, the alkylation agent is an alkylaluminum compound, preferably a $C_1$-$C_{20}$ alkylaluminum compound, more preferably a $C_4$-$C_{18}$ alkylaluminum compound. The alkyl group of the general formula $C_nC_nH_{2n+1}$ where $n \geq 1$ may be linear, branched, or cyclic. In a preferred embodiment, the alkylation agent is a trialkylaluminum compound. Suitable trialkylaluminum compounds may include, for example, trimethylaluminum, triethylaluminum, tri-n-propyl aluminum, triisopropylaluminum, tri-n-butylaluminum, triisobutylaluminum, tri(2,4,4,-trimethylpentyl)-aluminum, trioctylaluminum, tridecylaluminum, tridodecylaluminum, trihexadecylaluminum, trioctadecylaluminum, dimethylaluminum chloride, methylaluminum dichloride, diethylaluminum chloride, ethylaluminum dibromide, etc. In a preferred embodiment, the trialkylaluminum compound is tri-n-butylaluminum or tri-n-octylaluminum. Additionally, the alkylaluminum compound may be employed in the form of an ether adduct. For example, the trialkylaluminum compound may be complexed with an ether donor, such as dibutyl ether.

In another embodiment of the present invention, the alkylation agent is an alkylmagnesium compound, preferably a $C_1$-$C_{20}$ alkylmagnesium compound. More specifically, the alkylation agent may be an alkylmagnesium halide compound, preferably a $C_4$-$C_{18}$ alkylmagnesium halide compound. The halide may be selected from the group consisting of fluoride (F), chloride (Cl), bromide (Br), iodide (I), and astatide (At), preferably chloride (Cl), bromide (Br), or iodide (I). In a preferred embodiment, the halide is chloride. For example, the alkylmagnesium halide compound may be n-butylmagnesium chloride or n-octylmagnesium chloride.

Figure 3:
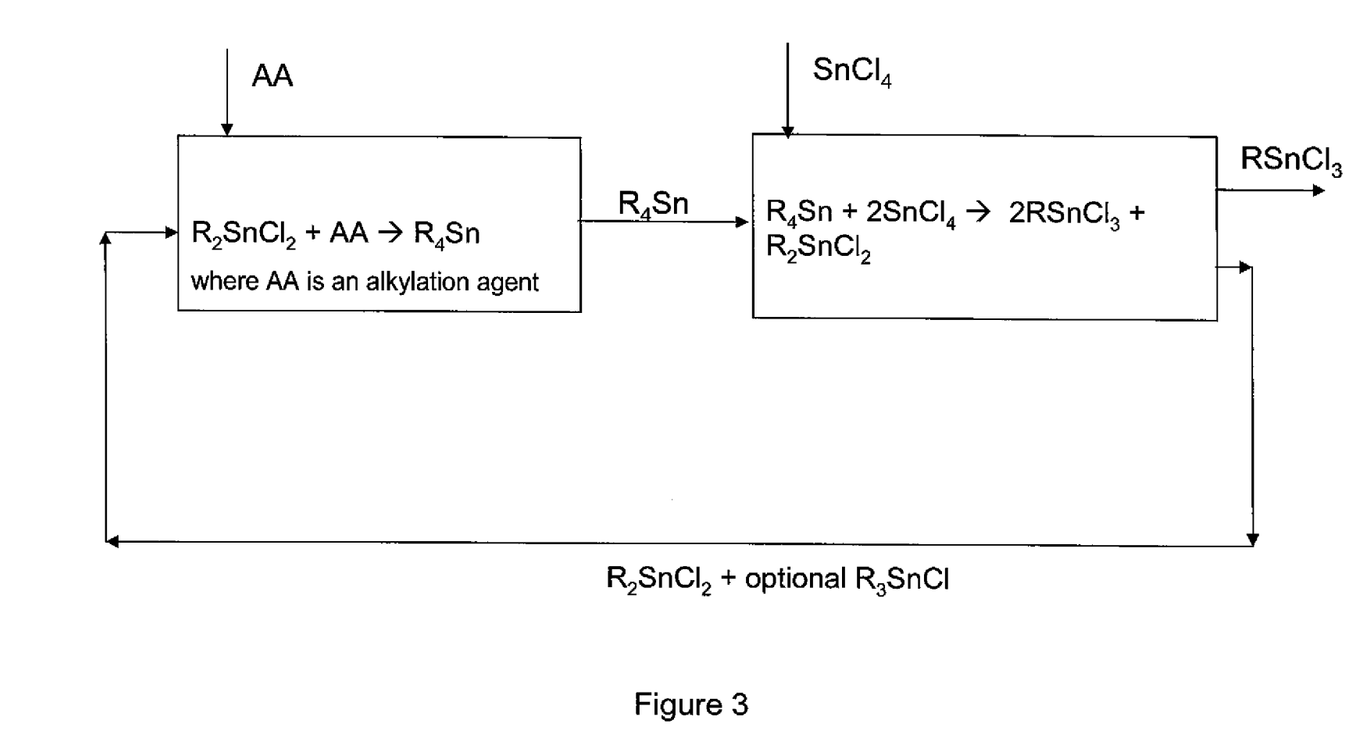
FIG. 3 shows an embodiment of the present invention that does not add any tin tetrahalide in the first alkylation step.

The dialkyltin dihalide and alkylation agent may be contacted in any suitable manner using any suitable methods known in the art to cause partial or complete reaction of the reactants to form a tetraalkyltin product. For example, each of the reactants may be charged to a reactor and agitated to form a homogenous mixture or the reactants may be added dropwise in any suitable order. As would be recognized by one skilled in the art, unreacted reactants may be present and/or other products or by-products may also be formed. In one embodiment, the dialkyltin dihalide may be reacted solely with an alkylation agent to form the tetraalkyltin compound. For example, as shown in FIG. 3, dialkyltin dichloride may be reacted with an alkylation agent, such as alkyl magnesium chloride, to form a tetraalkyltin compound.

Alternatively, the dialkyltin dihalide and alkylation agent may also be contacted and reacted with a tin tetrahalide to form the tetraalkyltin product. The halide in tin tetrahalide may be fluoride, chloride, bromide, iodide, or astatide. For example, the tin tetrahalide may be tin tetrachloride, also known as stannic chloride, with the formula $SnCl_4$ or tin(IV) iodide, also known as stannic iodide, with the formula $SnI_4$. In a preferred embodiment, the tin tetrahalide is tin tetrachloride.

Additional reactants or ingredients may also be included with the dialkyltin dihalide, alkylation agent, and/or tin tetrahalide, such as a solvent or mixture of solvents. The solvent may be an inert organic solvent, such as hexane, isooctane, benzene, toluene, kerosene, cyclohexane, chlorobenzene, etc. A suitable Grignard solvent, e.g., an ether, such as tetrahydrofuran, diethylether, or dibutyl ether, may also be used. A catalyst may or may not be included in the reaction. In a preferred embodiment, no catalysts, such as a precious metal catalyst, are included in the reaction medium. The reaction temperature may be the same as used in conventional alkylation processes of tin tetrahalides. In other words, the preferred reaction temperature for the alkylation step may depend on the alkylation agent used. For example, the reaction does not need to be conducted at high temperatures. In particular, the reaction temperature in the first alkylation step may be controlled such that the temperature is maintained at or below 70° C., for example, for alkylaluminum compounds.

The dialkyltin dihalide, alkylation agent, and tin tetrahalide may be contacted and reacted in any suitable manner or order using any suitable methods known in the art to cause partial or complete reaction of the reactants to form the tetraalkyltin product, other products or by-products, such as trialkyltin halide or dialkyltin dihalide, and any unreacted reactants. For example, the dialkyltin dihalide may react with the alkylation agent and the tin tetrahalide may react with the alkylation agent to form the tetraalkyltin compound. In the case of chloride as the halide, the reaction may be depicted as follows:

$R_2SnCl_2$+alkylation agent+$SnCl_4 \rightarrow R_4Sn+R_3SnCl+$ 
$R_2SnCl_2$ where R is $C_nC_nH_{2n+1}$, and $n \geq 1$.

Figure 4:
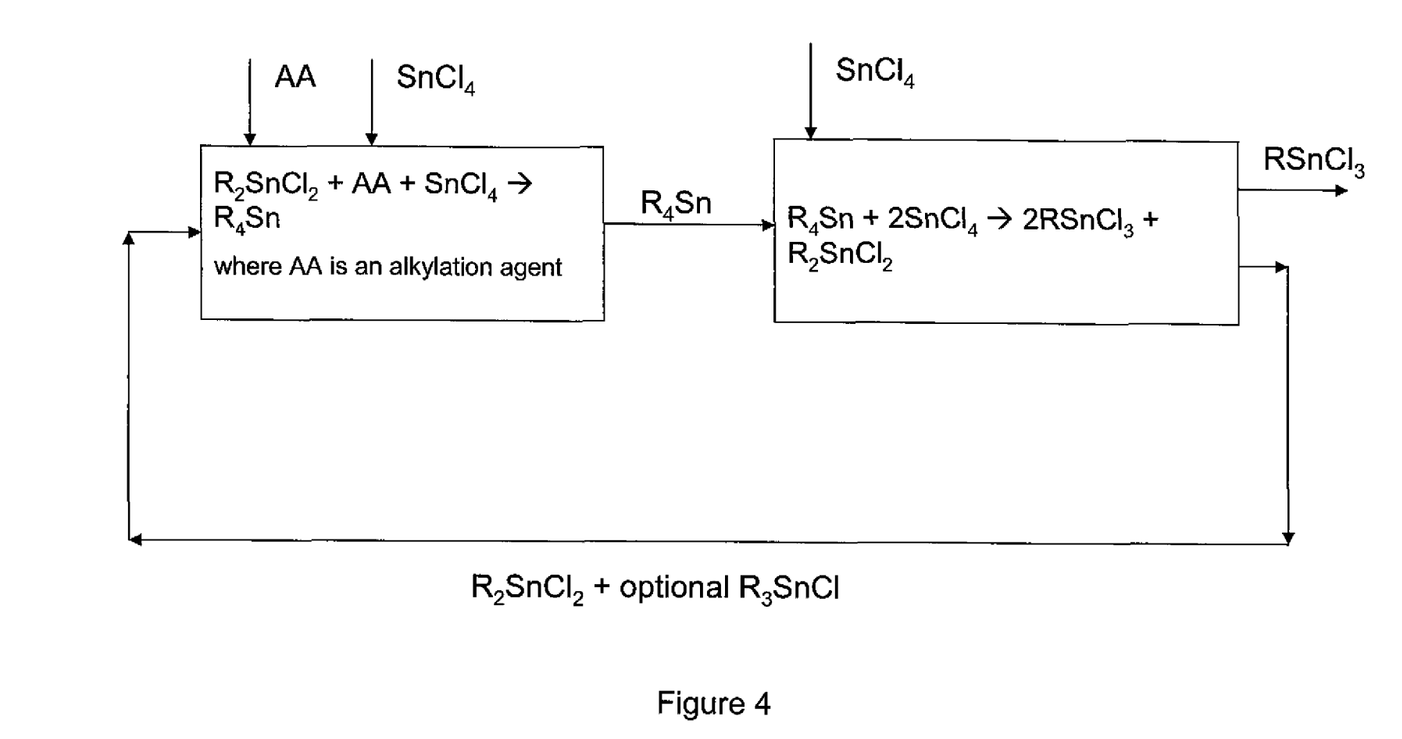
FIG. 4 shows an embodiment of the present invention where tin tetrachloride is added in the first alkylation step.

The reaction product is a tetraalkyltin mixture comprising at least tetraalkyltin, and may contain trialkyltin halide, and dialkyltin dihalide as minor products. For example, as shown in FIG. 4, dialkyltin dichloride and tin tetrachloride may be reacted with an alkylation agent, such as alkyl magnesium chloride, to form the tetraalkyltin compound. The reaction product may be treated to remove any unwanted by-products and/or solvent, for example, resulting from the alkylation agent (e.g., Al or Mg compounds).

Figure 2:
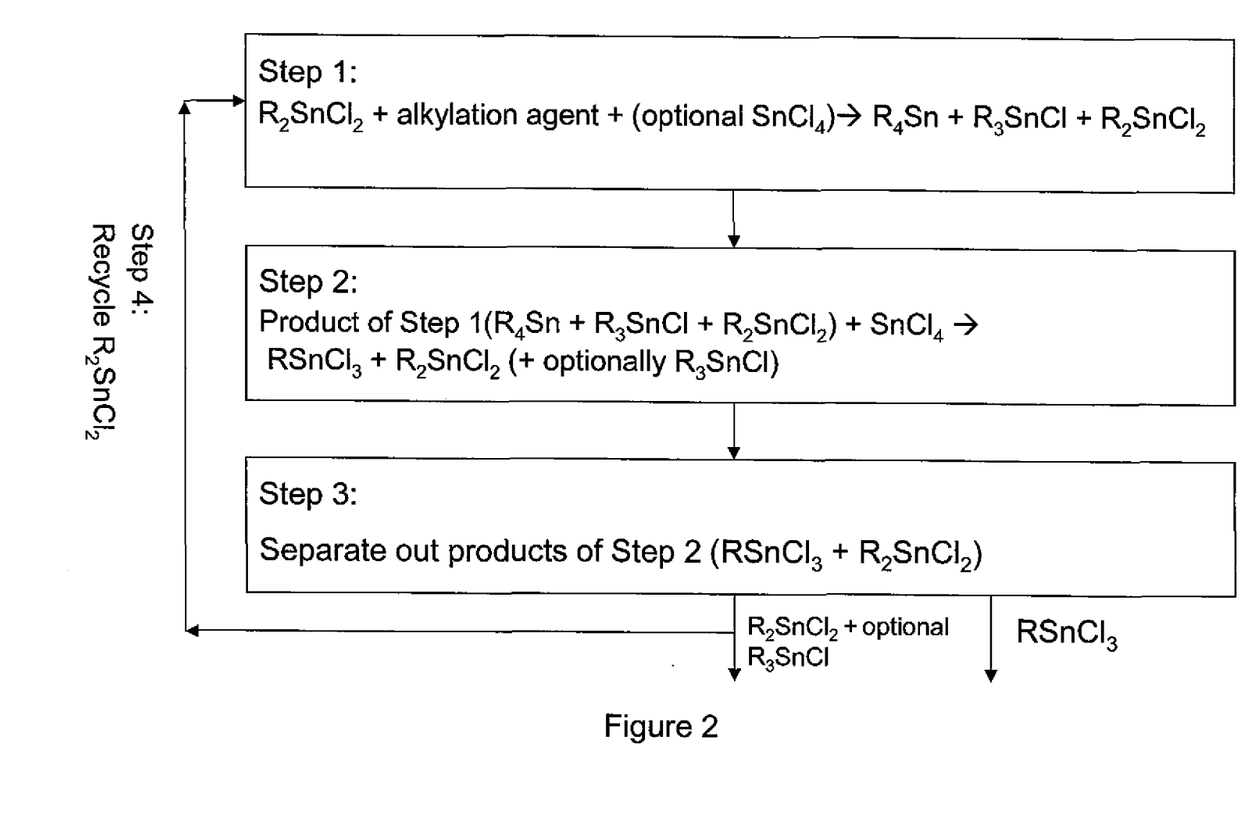
FIG. 2 depicts another embodiment of the present invention showing a four step cyclic process for producing a high yield and high purity monoalkyltin trichloride.

Second, the tetraalkyltin mixture is reacted with tin tetrahalide to form a monoalkyltin trihalide mixture comprising at least monoalkyltin trihalide and dialkyltin dihalide as shown in step 2 in FIGS. 1 and 2. This monoalkyltin trihalide mixture may also optionally contain trialkyltin halide. In some embodiments the amount of trialkyltin halide is present in trace amount. In other embodiments, the amount of trialkyltin halide is present in higher amounts, for example greater than 1 mol %, greater than 5 mol % or from 0.5 to 25 mol % based on total moles of tin in the monoalkyltin trihalide mixture.

The initial tin compound, tin tetrahalide, is used as starting material, which is transformed into the alkyltin halide compounds. Any suitable type and amount of tin tetrahalide compound may be used from any suitable source. The tin tetrahalide may be used neat or pre-dissolved in a solvent, e.g., alkanes, such as hexanes, or aromatics, such as toluene. Any halide described herein may be selected, but Cl, Br, and I are preferred. In a more preferred embodiment, the tin tetrahalide is tin tetrachloride.

Additional reactants or ingredients may also be included with the tetraalkyltin mixture and tin tetrahalide, such as a solvent or mixture of solvents. Any of the solvents listed in step 1 may be suitable, although ethers are less preferred. A catalyst may or may not be included in the reaction. In a preferred embodiment, no catalysts, such as a precious metal catalyst, are included in the reaction medium. The reaction may be conducted at any suitable temperature. In particular, it is preferred that the reaction temperature in the second disproportionation step is controlled such that the temperature is maintained at or below 150° C. in order to reach high yields. More preferably, the rate of addition of tin tetrahalide may be controlled such that the exotherm produced does not exceed 135° C.

As shown in FIG. 1, the product of the first step, e.g., $R_4Sn+R_3SnX+R_2SnX_2$, is reacted with the tin tetrahalide to form the monoalkyltin trihalide.

Dialkyltin dihalide is also formed. Optionally, trialkyltin halide may be present in this monoalkyltin trihalide mixture as previously mentioned. The reaction may be depicted as follows:

$R_4Sn+R_3SnX+R_2SnX_2+SnX_4 \rightarrow RSnX_3+R_2SnX_2$ with R being $C_nC_nH_{2n+1}$, $n \geq 1$, and X is a halide. As would be recognized by one skilled in the art, unreacted reactants and/or other products or by-products may also be present in the reaction product thereby obtained. It is envisioned that the first step (a) and the second step (b) may be conducted sequentially or simultaneously by proper choice of the reaction conditions. If conducted simultaneously, sufficient reactants may be provided to allow for at least partial completion of both reactions. It is preferred, however, that steps (a) and (b) are conducted sequentially, where step (a) is conducted first and the products of step (a) are introduced to step (b). The two-step process is more efficient and provides for the production of lower levels of trialkyltin halide and dialkyltin dihalide.

A tetra-alkyltin/trialkyltin halide mixture may be first produced using Grignard or alkylaluminum chemistry which, after suitable work-up, is then further reacted in a disproportionation reaction with stannic halide to arrive at the desired dialkyltin dihalide/mono-alkyltin trihalide mixture. Using this method, without recycling, the dialkyltin dihalide results in a maximum amount of monoalkyltin trihalide that can be obtained in the product stream ranging from about 60 to 67 mole % depending on the tetra-alkyltin content that was obtained in the first step.

It was found that by recycling the dialkyltin dihalide, however, monoalkyltin trihalide is directly produced in this step with little or no trialkyltin halide if desired. In other words, only trace amounts of trialkyltin halide, as an impurity, can be produced and recovered with the dialkyltin dihalide. Thus, the portion of dialkyltin dihalide produced that is not needed as a raw material is re-alkylated in the first step either alone or, in case of a partial recycle, by co-feeding it with tin tetrahalide. This process allows for a high yield of at least 60 to 99% of tin in the tetrahalide starting material to be converted into monoalkyltin trihalide and, in a case of at least partial recycle, simultaneously produces dialkyltin dihalide with less than 1 mole % trialkyltin halide. In one embodiment, 60 to 99 mole % of the tin tetrahalide in step (b) is converted into monoalkyltin trihalide. In another embodiment, 60 to 99 mole % of the tin tetrahalide introduced in both step (a) and step (b) is converted into monoalkyltin trihalide.

Third, the monoalkyltin trihalide mixture is processed to separately recover the monoalkyltin trihalide and a dialkyltin dihalide stream containing the dialkyltin dihalide as shown in step 3 in FIGS. 1 and 2. Any suitable processing can be employed to separate and recover the monoalkyltin trihalide and the dialkyltin dihalide, respectively. For example, a suitable separation process may include a distillation step, such as a continuous or batch distillation process, or an aqueous extraction. Any trialkylin halide may be recovered with the dialkyltin dihalide or may be additionally processed and recovered separately. In some embodiments, the dialkyltin dihalide recovered in step (c) contains less than 5 mole % trialkyltin halide or in other embodiments less than 1 mol % as an impurity based on total moles of tin in the dialkyltin dihalide stream. In other embodiments, it is possible to have higher levels of trialkylin halide in the dialkyltin dihalide stream, such as for example 5 to 90 mol % or 5 to 50 mol % trialkyltin halide based on the total moles of tin in the dialkyltin dihalide stream. The dialkyltin dihalide may be either isolated completely or partly from the reaction medium and reused at the beginning of a new reaction cycle to produce again monoalkyltin trihalides or mixtures of monoalkyltin trihalides and dialkyltin dihalides.

Thus, in the final step, at least a portion of the dialkyltin dihalide stream recovered in the third step (c) is recycled to the first contacting step as shown as step 4 in FIGS. 1 and 2. As used herein, recycle, reused, and/or cyclic processes may be used to signify that all or a part of the products obtained in the process will be reintroduced in a previous step of the same process but in a subsequent cycle.

Some or all of the recycled dialkyltin dihalide may be re-alkylated in the first step with the alkylation agent either alone or, in the case of a partial recycle, by co-feeding it with the tin tetrahalide. Any amount of dialkyltin dihalide may be recycled as necessary to achieve the optimal conversion of tin tetrahalide to monoalkyltin trihalide. The recycle stream may include a "single" recycle of the dialkyltin dihalide, for example, in a batch process where only a single quantity of dialkyltin dihalide produced in the batch is recycled. The recycle stream may also include "multiple" or "continuous" recycling of the dialkylin dihalide, for example, ongoing recycling may occur in a continuous process. In one embodiment, more than one cycle occurs in recycling the dialkyltin dihalide recovered in step (c) to the contacting step (a). In another embodiment of the present invention, all of the dialkyltin dihalide produced is recycled to the first contacting step (a). The appropriate amount to be recycled may be determined based on commercial demand for products made from dialkyltin dihalide or a mixture of monoalkyltin trihalide and dialkyltin dihalide. The present invention is advantageous in that the amount recycled is not dependent on a fixed amount of recycled dialkyltin dichloride and allows the portion of dialkyltin dihalide produced in step (b) that is not needed to produce end-products to be recycled.

With respect to the overall mono-alkyltin trihalide yield, it is only limited by the efficiency of the separation between mono-alkyltin trihalide and di-alkyltin dihalide after step (b) and the yield of the alkylation step (a). Yields of nearly 100% are possible if the efficiencies of both steps (a) and (b) approach 100%. The separation efficiency of the separation step, the amount of monoalkyltin trihalide left in the dialkylin dihalide rich stream of the separation step, and the concentration of the dialkyltin dihalide in the dialkyltin dihalide rich product stream determine the maximum amount of the dialkyltin dihalide rich fraction that can be recycled. Monoalkyltin trihalide is also alkylated to tetraalkyltin, for example, according to the following equations:

If the amounts of dialkyltin dichloride and mono-alkyltin trichloride that are being recycled to tetra-alkyltin are not sufficient to maintain a steady state condition, for example, because the di-alkyltin dichloride stream is needed for other downstream products or because the yield of the alkylation step is low, then additional tin tetrachloride can be added in the alkylation step to compensate for the loss of Sn. By careful choice of the separation efficiency between mono-alkyltin trihalide and di-alkyltin dihalide and the proportion of dialkyltin dihalide that is recycled, one can obtain monoalkyltin trihalide in 60 to nearly 100% yield and dialkyltin dihalide in nearly 0 to 40% yield on Sn.

In subsequent reaction cycles the tin tetrahalide in step (a) may be replaced fully or partially by dialkyltin dihalide that is recycled from the previous reaction cycle in order to obtain tetraalkyltin for step (b). It is envisioned that alkylation during step (a) may not be complete and a mixture of tetralkyltin and trialkyltin halide may be produced. This may especially be the case if alkyl aluminum is used as the alkylation agent. It may be desirable to perform an incomplete alkylation, for example, by deficiency in Grignard reagent, in order to improve the yield from the alkylating agent. This may be beneficial, for example, for raw material costs and efficiency and decreasing emissions.

In contrast to the conventional processes for producing alkyltin halides, a high yield, high purity monoalkyltin trihalide may be obtained. The conventional processes produce a maximum theoretical amount of monoalkyltin halide of 67 mole %, but in practice this is typically limited to 60 mole % or less. Thus, by utilizing the full or partial recycling of the dialkyltin dihalide obtained in the cyclic process, the maximum amount of monoalkyltin trihalide that may be obtained in the product stream ranges from 60 to nearly 100 mole %, more specifically from 70 to 99 mole %. For example, a 60:40 molar ratio (60 mole % monoalkyltin halide and 40 mole % dialkyltin dihalide) may be targeted for step (b) because that ratio is optimized for the reaction to simultaneously minimize the amounts of trialkylin halide and unreacted tin tetrahalide impurities, e.g., $SnCl_4$, at the end of the reaction. It is desirable to minimize the amounts of tin tetrahalide to reduce any detrimental effects on the downstream process in producing end-products derived from monoalkyltin trihalides, dialkyltin dihalides, and their mixtures and the performance of the end-products in use. Moreover, the amount of trialkyltin halide produced can be minimized, if desired, which lessens the toxicity. If the dialkyltin dihalide is intended to be used as a raw material in subsequent manufacturing processes (as opposed to being recycled), it is desired to have little to no trialkyltin halide because the trialkyltin halides are generally significantly more toxic than dialkyltin dihalides. Accordingly, the amount of trialkyltin halide is preferably less than 1 mole % in the dialkyltin dihalide stream for such applications.

In an embodiment of present invention, a monoalkyltin trihalide may be produced by first contacting dialkyltin dihalide with an alkylation agent and, optionally, tin tetrahalide, to form a tetraalkyltin mixture comprising tetraalkyltin, trialkyltin halide, and dialkyltin dihalide. Second, reacting the tetraalkyltin mixture with tin tetrahalide to form a monoalkyltin trihalide mixture comprising monoalkyltin trihalide, dialkyltin dihalide and optionally trialkyltin halide. Third, processing the monoalkyltin trihalide mixture to separately recover the monoalkyltin trihalide and a dialkyltin dihalide stream containing the dialkyltin dihalide, and finally, recycling at least a portion of the dialkyltin dihalide stream recovered in the third step to the first contacting step.

In the case where R=butyl and X is chloride, the following process may occur. Monobutyltin trichloride or mixtures of monobutyltin trichloride and dibutyltin dichloride may be formed by contacting dibutyltin dichloride with an alkylation agent and, optionally, tin tetrachloride, to form a tetrabutyltin mixture comprising at least tetrabutyltin and tributyltin chloride and dibutyltin dichloride as possible minor products. Next, the tetrabutyltin mixture is reacted with tin tetrachloride to form a monobutyltin trichloride mixture comprising monobutyltin trichloride, dibutyltin dichloride and optionally tributyltin chloride. Subsequently, the monobutyltin trichloride mixture is processed to separately recover the monobutyltin trichloride and a stream containing the dibutyltin dichloride and optionally tributyltin chloride. Finally, at least a portion of the dibutyltin dichloride stream recovered is recycled to the contacting step where dibutyltin dichloride is contacted with an alkylation agent and, optionally, tin tetrachloride.

In the case where R=octyl and X is chloride, the following process may occur. Monooctyltin trichloride or mixtures of monooctyltin trichloride and dioctyltin dichloride may be formed by contacting dioctyltin dichloride with an alkylation agent and, optionally, tin tetrachloride, to form a tetraoctyltin mixture comprising at least tetraoctyltin and trioctyltin chloride and dioctyltin dichloride as possible minor products. Next, the tetraoctyltin mixture is reacted with tin tetrachloride to form a monooctyltin trichloride mixture comprising monooctyltin trichloride, dioctyltin dichloride and optionally trioctyltin chloride. Subsequently, the monooctyltin trichloride mixture is processed to separately recover the monooctyltin trichloride and a stream containing the dioctyltin dichloride and optionally trioctyltin chloride. Finally, at least a portion of the dioctyltin dichloride stream recovered is recycled to the contacting step where dioctyltin dichloride is contacted with an alkylation agent and, optionally, tin tetrachloride.

The monoalkyltin trihalides, dialkyltin dihalides, and mixtures of the monoalkyltin trihalides and dialkyltin dihalides made according to the processes described herein may be used as intermediates for PVC stabilizers, glass coating chemicals, catalysts or catalyst precursors, for example.

EXAMPLES

Example 1

Monobutyltin Trichloride and Dibutyltin Dichloride Synthesis Using tri-n-Butylaluminum as the Alkylating Agent First, dibutyl ether is charged to a reaction flask and inerted with nitrogen. Based on the amounts of dibutyltin dichloride and tin tetrachloride, the amount of tri-n-butylaluminum required to produce an 85:15 mixture of tetrabutyltin and tributyltin chloride is charged to the reaction flask and agitated to give a homogeneous mixture. Tin tetrachloride and dibutyltin dichloride are then added at a rate to keep the temperature of the reaction mixture below 70° C. After the end of addition, the mixture is agitated for 2 hours and cooled to about 20° C. Water is added in an amount to give a nearly saturated solution of aluminum trichloride, and the mixture agitated for 30 minutes. Agitation is stopped and the phases allowed to split for 1 hour. The aqueous phase is removed and the organic phase is vacuum stripped to remove residual water and the dibutyl ether solvent leaving a mixture of tetrabutyltin and tributyltin chloride.

Second, the mixture of tetrabutyltin and tributyltin chloride is inerted with nitrogen. Tin tetrachloride in an amount required to produce a 60:40 mixture of monobutyltin trichloride and dibutyltin dichloride is added to the reaction flask at such a rate that the exotherm does not exceed 135° C. After all the tin tetrachloride is added the mixture is agitated at 135° C. for 2 hours then cooled to <40° C.

Third, monobutyltin trichloride is then removed via vacuum distillation at 80° C. and 5 torr. After the monobutyltin trichloride has been removed, dibutyltin dichloride is distilled at 135° C. and 5 torr. The reaction flask is cooled to <40° C. and the vacuum broken with nitrogen.

Fourth, all or a portion of dibutyltin dichloride produced is used as the raw material feed in step 1.

Example 2

Monobutyltin Trichloride and Dibutyltin Dichloride Synthesis Using n-Butylmagnesium Chloride as the Alkylating Agent First, dibutyltin dichloride, and optionally tin tetrachloride, is dissolved in heptane under a dinitrogen atmosphere. A solution of n-butyl magnesium chloride ("BuMgCl) in tetrahydrofuran (THF) (1 molar equiv. to Sn—Cl) is added under stirring at a rate to keep the temperature of the reaction mixture below 70° C. After the end of the addition, the mixture is diluted with hexane and agitated for 2 hours under reflux. Ca. 25% of the THF is distilled off atmospherically. The mixture is cooled to about 20° C. and added with stirring to a 2.4 wt % solution of hydrochloric acid (HCl) in water in an amount to give a nearly saturated solution of $MgCl_2$. After stirring for 15 min and cooling to about 20° C., agitation is stopped and the phases are allowed to split. The aqueous phase is removed and the organic phase is vacuum stripped to remove residual water and solvents leaving a mixture that is mainly tetrabutyltin with some tributyltin chloride.

Second, the mixture of tetrabutyltin and tributyltin chloride is inerted with dinitrogen. Tin tetrachloride, in an amount required to produce a 60:40 mixture of monobutyltin trichloride and dibutyltin dichloride, is added to the reaction flask at such a rate that the exotherm does not exceed 135° C. After all the tin tetrachloride is added, the mixture is agitated at 135° C. for 2 hours and then cooled to <40° C.

Third, monobutyltin trichloride is then removed via vacuum distillation at 138-141° C. and 50-70 torr. After the monobutyltin trichloride has been removed, dibutyltin dichloride is distilled at 168-169° C. and 25-35 torr. The reaction flask is cooled to <40° C. and the vacuum broken with dinitrogen.

Fourth, all or a portion of the dibutyltin dichloride obtained is used as the raw material feed in the first step.

Example 3

Monooctyltin Trichloride and Dioctyltin Dichloride with Recycling of Dioctyltin Dichloride to Tetraoctyltin using n-Octylmagnesium Chloride as the Alkylating Agent Disproportionation A 1 L three-necked flask was charged with a "$Oct_4Sn$ reaction product (400 g obtained from a previous cycle, $Oct_4Sn$, 87.8 wt %; $Oct_3SnCl$, 2.5 wt %; $Oct_2SnCl_2$, 1.6 wt %), inerted and heated to 75° C. $SnCl_4$ (325 g, 1.25 mol, corresponding to two equiv. on $Oct_4Sn$ and one equiv. on $Oct_3SnCl$) was slowly added and the resulting dark suspension was heated further to 130° C. and stirred for two hours at this temperature. A sample was taken from the mixture, butylated and analyzed by gas chromatography. Part of the $^n$OctSnCl$_3$ was fractionally distilled from the mixture at 15-18 mbar, 157-158° C. The purity and composition of the distillate and distillation residue were determined by gas chromatographic analysis after alkylation with BuMgCl. The results are listed in Tables 3 and 4 (cycle 3).

n-Octylmagnesium chloride

A 2 L three-necked flask was equipped with a dropping funnel and cooler, inerted and charged with 46.2 g of fresh magnesium turnings (1.90 mol) and approx. 2 g of magnesium turnings that originated from a previous octyl-Grignard synthesis. A solution of 265 g (1.78 mol) of 1-chlorooctane and 475 g of THF was prepared and charged to the dropping funnel. Next, 125 g of THF was added to the flask, followed by 17.0 g (0.11 mop of 1-chlorooctane. The resulting mixture was gently heated until the reaction started (at ca. 40° C.). The pot temperature increased to 67° C. Then, addition of the remaining octylchloride solution was started at a rate to maintain gentle reflux. After ca. 45 minutes the addition was complete, and the resulting mixture was refluxed for another 60 minutes. The resulting suspension was left to settle overnight and the supernatant was decanted and stored for further use. The titer of the Grignard solution was analyzed using acid-base titration: expected, 2.05 mol/kg; found, 1.95 mol/kg.

Tetra(n-octyl)tin

A dioctyltin chloride (DOTC)/monooctyltin chloride (MOTC) mixture (51.6 g, 153 mmol of MOTC and 246 g, 591 mmol of DOTC, 744 mmol of Sn) was charged into a 2 L three-necked flask, equipped with dropping funnel, mechanical stirrer, and cooler. The dropping funnel was charged with 840 g of n-octylmagnesium chloride solution (1.95 mol/kg in THF; 1.64 mol). The octyltin mixture was melted by heating to 50° C., heptane (86 g) was added and addition of the Grignard solution was started. The rate of addition was adjusted to maintain a pot temperature below 70° C. (total addition time ca. 90 min.). After the addition was complete, the dropping funnel was rinsed with 150 g of heptane and the resulting thick suspension was refluxed for another 2 h. (T=76° C.). Next, 190 g of solvent was distilled off at atmospheric pressure ($T_{vap}$=64° C.). The resulting residue was cooled to below 30° C. and then slowly added to a 2 L beaker containing 350 g of water and 25.5 g of 36% hydrochloric acid under vigorous stirring. The resulting biphasic system was stirred for 15 minutes and then left to settle. The aqueous phase was removed and the remaining organic phase was concentrated in vacuo to afford 439 g of brown liquid that was analyzed by gas chromatography after alkylation with BuMgCl. Results are collected in Table 2 (cycle 3).

A total of 4 cycles was completed following similar procedures. The first cycle was started using Oct$_4$Sn obtained from a commercial source. The series of cycles was complete with a partial fifth cycle to convert the Oct$_2$SnCl$_2$-rich residue of cycle 4 back to Oct$_4$Sn. The results are collected in Tables 2-4.

TABLE 2

Composition of the tetraoctyltin used as starting material in each cycle and its preparation from the dioctyltin dichloride-rich fractions obtained in cycles 1-3 (alkylation using RMgCl).

| Cycle (n) | Yield on Sn (%) | Composition of product mixture (wt %) | | | |
|---|---|---|---|---|---|
| | | Oct$_4$Sn | Oct$_3$SnCl | Oct$_2$SnCl$_2$ | Others[b] |
| 1[a] | — | 95.0 | — | — | — |
| 2 | 96.4 | 96.0 | 1.6 | 0.0 | 2.4 |
| 3 | 98.6 | 87.8 | 2.5 | 1.6 | 8.1 |
| 4 | 97.9 | 93.8 | 1.8 | 1.2 | 3.2 |
| 5[c] | 98.6 | 91.7 | 2.3 | 3.8 | 2.1 |

[a]A commercial grade of Oct$_4$Sn was used as starting material for the first cycle.
[b]Volatiles not containing tin.
[c]Only the reaction to tetraoctyltin was performed.

TABLE 3

Results of the disproportionation of tetraoctyltin with tin tetrachloride.

| Cycle (n) | Composition of product mixture (wt %) | | | |
|---|---|---|---|---|
| | Oct$_3$SnCl | Oct$_2$SnCl$_2$ | OctSnCl$_3$ | SnCl$_4$ |
| 1 | 0.7 | 38.3 | 60.3 | 0.7 |
| 2 | 0.2 | 37.8 | 61.1 | 0.9 |
| 3 | 0.7 | 38.8 | 59.9 | 0.6 |
| 4 | <0.1 | 38.8 | 59.1 | 2.1 |

TABLE 4

Distillation of OctSnCl$_3$ from the OctSnCl$_3$/Oct$_2$SnCl$_2$ mixtures after disproportionation

| Cycle (n) | Distillate (wt %) | | Composition of residue (wt %) | | |
|---|---|---|---|---|---|
| | Purity of OctSnCl$_3$ | Amount of OctSnCl$_3$ distilled | Oct$_2$SnCl$_2$ | OctSnCl$_3$ | Oct$_3$SnCl |
| 1 | 94.1 | 82 | 82.2 | 17.3 | <0.1 |
| 2 | 98.3 | 75 | 73.3 | 25.9 | <0.1 |
| 3 | 98.0 | 83 | 82.0 | 17.2 | <0.3 |
| 4 | 96.7 | 75 | 77.1 | 21.8 | <0.1 |

From the data obtained over the 4 cycles it became possible to calculate a cumulative mole balance and to compare the yields on Sn with theoretical predictions for the yield of RSnCl$_3$ ($Y_m(n)$) and R$_2$SnCl$_2$ ($Y_d(n)$) as a function of the number of cycles (n) (Tables 5 and 6). The following definitions are used:

Cumulative yield of RSnCl$_3$($Y_m$(n))=(cumulative amount of OctSnCl$_3$ distilled)/(cumulative amount of SnCl$_4$ used as starting material+cumulative amount of R$_4$Sn used as starting material), all values in moles.

Distillation yield of RSnCl$_3$ ($Y_{dest}$(n))=(cumulative amount of RSnCl$_3$ distilled)/(cumulative amount of RSnCl$_3$ present in the reaction mixture after the disproportionation reaction), all values in moles.

Theoretical yield of RSnCl$_3$($Y_{m,theor}$(n))=(($\Sigma Y_{dest}$(n)× 2)/n)/(2+1/n).

Cumulative yield of $R_2SnCl_2$ ($Y_d(n)$)=(cumulative amount of $Oct_2SnCl_2$ in the part of the distillation residue that is not recycled to $R_4Sn$)/(cumulative amount of $SnCl_4$ used as starting material+cumulative amount of $R_4Sn$ used as starting material), all values in moles.

Theoretical yield of $R_2SnCl_2$($Y_{d,theor}(n)$)=$(\Sigma(1-1/(1+2\times(1-Y_{dest}(n))))/n)/(2+1/n)$.

$\Sigma$ signifies summation over all reaction cycles n.

From Table 4 and 6 it can be concluded that the new procedure can afford $RSnCl_3$ in up to 69% yield on Sn in 94-98% purity whereas only 55% yield on Sn would have been achievable if $R_2SnCl_2$ had not been recycled.

Accordingly $R_2SnCl_2$ was obtained in 12% yield on Sn after 4 cycles in 73%-82% purity with the concentration of $R_3SnCl$ relative to $R_2SnCl_2$ well below 1 mol %. A 33% yield of $R_2SnCl_2$ on Sn would have been obtained if $R_2SnCl_2$ had not been recycled.

Under steady-state conditions, the maximum amount of $R_2SnCl_2$ that can be recycled to $R_4Sn$ is limited by the amount of $RSnCl_3$ that remains in the distillation residue. This is because $RSnCl_3$ is also alkylated to $R_4Sn$.

There is a close correlation between $Y_m(n)$ and $Y_{m,theor}(n)$. The maximum $Y_m(n)$ achievable, predicted by $Y_{m,theor}(n)$, is dictated by the distillation yield $Y_{dest}(n)$. This can be easily envisioned by comparing $Y_{m,theor}(n)$ which becomes equal to $Y_{dest}(n)$ at high values of n (Table 6, column 4). At high values of n (n>50) $Y_m(n) \geq 78\%$ become possible with a maximum value of 78.7%.

There is an inverse but not proportional relationship between $Y_d(n)$ and $Y_{dest}(n)$ that can be approximated at high values of n by $Y_d(n)=(1-1/(1+2\times(1-Y_{dest}(n))))/2$ (Table 6, column 6). At the demonstrated $<Y_{dest}>=78.7\%$ the $R_2SnCl_2$ yield on Sn is expected to stabilize at 15% for high values of n (n>25). This is significantly lower than the 33% yield on $R_2SnCl_2$ that would be obtained if no $R_2SnCl_2$ was recycled.

TABLE 5

| Mole balance (R = $^n$Oct, alkylation using RMgCl) | | | | |
|---|---|---|---|---|
| Cycle | In (moles) | | | Part of $R_2SnCl_2$ fraction |
| (n) | $R_4Sn$ | $SnCl_4$ | Total Sn | recycled to $R_4Sn$ |
| 1 | 0.772[a] | 1.547 | 2.319 | 69.5% |
| 2 | 0.667[b] | 1.359 | 2.026 | 66.1% |
| 3 | 0.657[b] | 1.248 | 1.905 | 80.3% |
| 4 | 0.681[b] | 1.317 | 1.998 | 80.5% |

| | Out (moles) | | | | | |
|---|---|---|---|---|---|---|
| Cycle | $RSnCl_3$ in distillate | $R_2SnCl_2$ fraction not used for recycling to $Oct_4Sn$ | | | | Total |
| (n) | $RSnCl_3$ | $R_2SnCl_2$ | $RSnCl_3$ | $SnCl_4$ | $R_3SnCl$ | Sn |
| 1 | 1.269 | 0.244 | 0.063 | 0.002 | — | 2.245 |
| 2 | 1.017 | 0.236 | 0.103 | 0.003 | — | 2.015 |
| 3 | 1.061 | 0.135 | 0.035 | 0.001 | 0.0004 | 1.913 |
| 4 | 0.976 | 0.137 | 0.048 | 0.003 | — | 1.927 |

[a]Obtained from a commercial source.
[b]Obtained by alkylation of the distillation residue of the previous cycle.

TABLE 6

| | Distillate | | | Distillation residue | |
|---|---|---|---|---|---|
| Cycle (n) | Cumulative yield of $RSnCl_3$ on Sn ($Y_m(n)$)[a] | Proportion of $RSnCl_3$ distilled ($Y_{dest}(n)$)[b] | Theoretical cumulative yield of $RSnCl_3$ on Sn ($Y_{m,theor}(n)$)[c] | Cumulative yield of $R_2SnCl_2$ on Sn ($Y_d(n)$)[d] | Theoretical cumulative yield of $R_2SnCl_2$ on Sn ($Y_{d,theor}(n)$)[e] |
| 1 | 54.7% | 81.8% | 54.5% | 10.5% | 8.9% |
| 2 | 62.2% | 75.0% | 62.7% | 13.0% | 12.0% |
| 3 | 67.9% | 82.6% | 68.4% | 12.5% | 12.3% |
| 4 | 69.2% | 75.4% | 70.0% | 12.0% | 13.2% |
| 10 | | | 75.0% | | 13.5% |
| 100 | | | 78.4% | | 14.8% |
| ∞ | | | 78.7%[f] | | 14.9%[f] |

Yield calculations (R = $^n$Oct, alkylation using RMgCl)

[a]$Y_m(n)$ = (cumulative amount of $RSnCl_3$ distilled)/(cumulative amount of $SnCl_4$ used as starting material + cumulative amount of $R_4Sn$ used as starting material), all values in moles.
[b]$Y_{dest}(n)$ = (cumulative amount of $RSnCl_3$ distilled)/(cumulative amount of $RSnCl_3$ present in the reaction mixture after the disproportionation reaction), all values in moles.
[c]$Y_{m,theor}(n)$ = $((\Sigma Y_{dest}(n) \times 2)/n)/(2 + 1/n)$, the experimentally determined values for $Y_{dest}(n)$ were used.
[d]$Y_d(n)$ = (cumulative amount of $R_2SnCl_2$ in the part of the distillation residue that is not recycled to $R_4Sn$)/(cumulative amount of $SnCl_4$ used as starting material + cumulative amount of $Oct_4Sn$ used as starting material), all values in moles.
[e]$Y_{d,theor}(n)$ = $(\Sigma(1 - 1/(1 + 2 \times (1 - Y_{dest}(n))))/n)/(2 + 1/n)$, the experimentally determined values for $Y_{dest}(n)$ were used.
[f]The average of $Y_{dest}(n)$ over the 4 cycles was used ($Y_{dest}(n)$ = 78.7%).

Example 4

Monooctyltin Trichloride and Dioctyltin Dichloride from Tetraoctyltin followed by Alkylation of the Dioctyltin-containing Fraction to Tetraoctyltin using Tri(n-octyl)aluminium Disproportionation A round bottom flask was charged with 451 g of $^{n}Oct_{4}Sn$ (426 g, 746 mmol) and heated to 75° C. $SnCl_{4}$ (393 g, 1.509 mol) was added in 10 min during which the temperature increased to 125° C. The resulting dark suspension was stirred for 3 hours at 130° C. A sample of the liquid was butylated using excess of BuMgCl in THF followed by hydrolysis with $H_{2}SO_{4}$(aq) and the composition determined by gas chromatography. $SnCl_{4}$: 2.4 wt %, $^{n}OctSnCl_{3}$: 58.9 wt %, $^{n}Oct_{2}SnCl_{2}$: 38.8 wt %, $^{n}Oct_{3}SnCl$: <0.1 wt %, $Oct_{4}Sn$: <0.1 wt %. Another 5.0 g of the $^{n}Oct_{4}Sn$ (4.7 g, 8.3 mmol) was added to the mixture which was then stirred at 130° C. for another 1.5 hrs. Fractional distillation (160° C., 18 mbar) afforded $^{n}OctSnCl_{3}$ (376 g) and a residue (432 g) that solidified on cooling to room temperature. Results are collected in Table 7.

Tetra(n-octyl)tin $^{n}Oct_{3}Al$ (93.0 g, 254 mmol, 1.01 equiv. of Oct-Al per Sn—Cl) was placed in a round bottom flask that was cooled on a water bath. $Bu_{2}O$ (35.0 g, 269 mmol, 1.06 equiv. per Al) was added dropwise in ca 5 min. during which the temperature rose to 40° C. The $^{n}Oct_{2}SnCl_{2}/^{n}OctSnCl_{3}$ mixture (129 g) was placed in a round bottom flask that was cooled on a water bath. The $^{n}Oct_{3}AlPBu_{2}O$ solution was then added to the $^{n}Oct_{2}SnCl_{2}POctSnCl_{3}$ mixture in ca 40 min while the temperature of the reaction mixture rose to 60° C. The resulting grey suspension was stirred at 80° C. for another 60 minutes. After cooling to room temperature the mixture was added slowly to a stirred flask containing 82 g of water (the temperature increased to 55° C.). After cooling to room temperature, hexane (20 g) and water (10 g) were added and the organic phase was separated. Volatiles were removed in vacuo yielding 152 g of a light yellow turbid liquid. A sample of the liquid was butylated using excess of BuMgCl in THF followed by hydrolysis with $H_{2}SO_{4}$(aq) and the composition determined by gas chromatography. Results are collected in Table 8.

TABLE 7

Composition of the tetra-octyltin used as starting material in the first cycle and preparation from the di-octyltin dichloride-rich fractions obtained in cycle 1 (alkylation using $R_{3}Al$).

| | | Composition of product mixture (wt %) | | | |
|---|---|---|---|---|---|
| Cycle (n) | Yield on Sn (%) | $Oct_{4}Sn$ | $Oct_{3}SnCl$ | $Oct_{2}SnCl_{2}$ | Others[b] |
| 1[a] | — | 94.5 | — | — | — |
| 2[c] | 80.7 | 84.4 | 10.9 | 1.5 | 3.2 |

[a]A commercial grade of $Oct_{4}Sn$ was used as starting material for the first cycle.
[b]Volatiles not containing tin.
[c]Only the reaction to tetraoctyltin was performed.

TABLE 8

Distillation of $OctSnCl_{3}$ from the $OctSnCl_{3}/Oct_{2}SnCl_{2}$ mixtures after disproportionation

| | Distillate (wt %) | | Composition of residue (wt %) | | |
|---|---|---|---|---|---|
| Cycle (n) | Purity of $OctSnCl_{3}$ | Amount of $OctSnCl_{3}$ distilled | $Oct_{2}SnCl_{2}$ | $OctSnCl_{3}$ | $Oct_{3}SnCl$ |
| 1 | 98 | 72.2 | 72.7 | 25.0 | <0.1% |

From the data obtained, it became possible to calculate a mole balance and to compare the yields on Sn with theoretical predictions for the yield of $RSnCl_{3}$ ($Y_{1}(n)$) and $R_{2}SnCl_{2}$ ($Y_{d}(n)$) as a function of the number of cycles (n) (Tables 9 and 10). Next to the previously defined parameters n, $Y_{m}(n)$, $Y_{dest}(n)$, $Y_{m,theor}(n)$, $Y_{d}(n)$ (See example 3) the following parameters are defined to account for the lower efficiency of the alkylation by $R_{3}Al$ as compared to RMgCl:

$$Y_{d,theor}(n)=(\Sigma(1-1/(1+2[R_{4}Sn]_{0}+[R_{3}SnCl]_{0}+[R_{2}SnCl_{2}]_{0}-2([R_{4}Sn]_{0}+[R_{3}SnCl]_{0})Y_{dest}(n)/Y_{tetra})/(2[R_{4}Sn]_{0}+[R_{3}SnCl]_{0}+[R_{2}SnCl_{2}]_{0}+1/n)$$

$[R_{4}Sn]_{0}$, $[R_{3}SnCl]_{o}$ and $[R_{2}SnCl_{2}]_{0}$ are the respective molar concentration of each compound in the $R_{4}Sn$ recycle stream that was obtained after alkylation using $R_{3}Al$.

$Y_{tetra}$=Sn yield of $R_{4}Sn$ synthesis.

From Tables 8 and 10, it can be concluded that the new procedure can afford $RSnCl_{3}$ in 48% up to 72% yield on Sn in 98% purity whereas only 44% yield on Sn would have been achievable if $R_{2}SnCl_{2}$ had not been recycled.

Accordingly, $R_{2}SnCl_{2}$ can be obtained in less than 11% yield on Sn and in 74% purity with the concentration of $R_{3}SnCl$ relative to $R_{2}SnCl_{2}$ well below 1 mol %. A 33% yield of $R_{2}SnCl_{2}$ on Sn would have been obtained if $R_{2}SnCl_{2}$ had not been recycled.

Under steady-state conditions, the maximum amount of $R_{2}SnCl_{2}$ that can be recycled to $R_{4}Sn$ is limited by the amount of $RSnCl_{3}$ that remains in the distillation residue. This is because also $RSnCl_{3}$ is alkylated to $R_{4}Sn$.

The maximum $Y_{m}(n)$ achievable, predicted by $Y_{m,theor}(n)$, is dictated by the distillation yield $Y_{dest}(n)$. This can be easily envisioned by comparing $Y_{m,theor}(n)$ which becomes equal to $Y_{dest}(n)$ at high values of n (Table 9, column 4). At high values of n (n>50) $Y_{m}(n) \geq 72\%$ become possible with a maximum value of 72.2%.

There is an inverse but not proportional relationship between $Y_{d}(n)$ and $Y_{dest}(n)$. At the demonstrated $<Y_{dest}>=72.2\%$, the $R_{2}SnCl_{2}$ yield on Sn is expected to stabilize at 10% for high values of n (n>10). This value is affected by the relatively low Sn yield of the alkylation step ($Y_{tetra}=80.7\%$). $Y_{d}(n)$ is expected to increase to a maximum value of 19% if $Y_{tetra}$ would increase to 100%. This is still significantly lower than the 33% yield on $R_{2}SnCl_{2}$ that would be expected if $R_{2}SnCl_{2}$ was not recycled.

TABLE 9

Mole balance (R = $n$Oct, alkylation using R$_3$Al)

| Cycle (n) | In (moles) | | | Part of R$_2$SnCl$_2$ fraction |
|---|---|---|---|---|
| | R$_4$Sn | SnCl$_4$ | Total Sn | recycled to R$_4$Sn |
| 1 | 0.754$^a$ | 1.509 | 2.263 | 87.0% |

| Cycle (n) | RSnCl$_3$ in distillate | Out (moles) | | | | Total Sn |
|---|---|---|---|---|---|---|
| | RSnCl$_3$ | R$_2$SnCl$_2$ fraction not used for recycling to Oct$_4$Sn | | | | |
| | | R$_2$SnCl$_2$ | RSnCl$_3$ | SnCl$_4$ | R$_3$SnCl | |
| 1 | 1.089 | 0.098 | 0.041 | 0.0008 | <0.0001 | 1.988 |

$^a$Obtained from a commercial source.

TABLE 10

Yield calculations (R = $n$Oct, alkylation using R$_3$Al)

| | Distillate | | | Distillation residue | |
|---|---|---|---|---|---|
| Cycle (n) | Yield of RSnCl$_3$ on Sn ($Y_m$(n))$^a$ | Proportion of RSnCl$_3$ distilled ($Y_{dest}$(n))$^b$ | Theoretical cumulative yield of RSnCl$_3$ on Sn ($Y_{m,theor}$(n))$^c$ | Yield of R$_2$SnCl$_2$ on Sn ($Y_d$(n))$^d$ | Theoretical cumulative yield of R$_2$SnCl$_2$ on Sn ($Y_{d,theor}$(n))$^e$ |
| 1 | 48.1% | 72.2% | 48.2% | 4.3% | 6.8% |
| 5 | | | 65.2% | | 9.2% |
| 10 | | | 68.5% | | 9.7% |
| 100 | | | 71.9% | | 10.2% |
| ∞ | | | 72.2%$^f$ | | 10.2%$^f$ |

$^a Y_m(n)$ = (cumulative amount of OctSnCl$_3$ distilled)/(amount of SnCl$_4$ used as starting material + amount of Oct$_4$Sn used as starting material), all values in moles.
$^b Y_{dest}(n)$ = (cumulative amount of RSnCl$_3$ distilled)/(cumulative amount of RSnCl$_3$ expected in the reaction mixture after the disproportionation reaction), all values in moles.
$^c Y_{m,theor}(n) = ((\Sigma Y_{dest}(n) \times 2)/n)/(2 + 1/n)$, the experimentally determined value for $Y_{dest}(1)$ was used.
$^d Y_d(n)$ = (cumulative amount of R$_2$SnCl$_2$ in the part of the distillation residue that is not recycled to R$_4$Sn)/)/(amount of SnCl$_4$ used as starting material + amount of R$_4$Sn used as starting material), all values in moles.
$^e Y_{d,theor}(n) = (\Sigma(1 - 1/(1 + 2[R_4Sn]_0 + [R_3SnCl]_0 + [R_2SnCl_2]_0 - 2([R_4Sn]_0 + [R_3SnCl]_0)Y_{dest}(n))/Y_{tetra})/(2[R_4Sn]_0 + [R_3SnCl]_0 + [R_2SnCl_2]_0 + 1/n)$, $Y_{tetra}$ = Sn yield of R$_4$Sn synthesis, the experimentally determined value for $Y_{dest}(1)$ was used.
$^f Y_{dest}(n)$ = 72.2% was used.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A process for producing monoalkyltin trihalide comprising:
   a. contacting dialkyltin dihalide with an alkylation agent and, optionally, tin tetrahalide, to form a tetraalkyltin mixture comprising tetraalkyltin, trialkyltin halide, and dialkyltin dihalide;
   b. reacting the tetraalkyltin mixture with tin tetrahalide to form a monoalkyltin trihalide mixture comprising monoalkyltin trihalide, dialkyltin dihalide and optionally trialkyltin halide;
   c. processing the monoalkyltin trihalide mixture to separately recover the monoalkyltin trihalide and a dialkyltin dihalide stream comprising the dialkyltin dihalide and optionally trialkyltin halide; and
   d. recycling at least a portion of the dialkyltin dihalide stream recovered in step (c) to the contacting step (a).

2. A process according to claim 1, wherein 60 to 99 mole % of the tin tetrahalide in steps (a) and (b) is converted into monoalkyltin trihalide.

3. A process according to claim 1, wherein the dialkyltin dichloride stream recovered in step (c) contains less than 5 mole % trialkyltin chloride.

4. A process according to claim 1, wherein the dialkyltin dichloride stream recovered in step (c) contains less than 1 mole % trialkyltin chloride.

5. A process according to claim 1, wherein the halide is selected from the group consisting of fluoride (F), chloride (Cl), bromide (Br), iodide (I), and astatide (At).

6. A process according to claim 1, wherein the halide is chloride.

7. A process according to claim 1, wherein the alkyl comprises 1 to 20 carbon atoms.

8. A process according to claim 1, wherein the alkyl is a linear alkyl, a branched alkyl, or a cycloalkyl.

9. A process according to claim 1, wherein the alkylation agent is a trialkylaluminum compound.

10. A process according to claim 9, wherein the trialkylaluminum compound is tri-n-butylaluminum.

11. A process according to claim 9, wherein the trialkylaluminum compound is tri-n-octylaluminum.

12. A process according to claim 1, wherein the alkylation agent is a C$_1$-C$_{20}$ alkylaluminum compound.

13. A process according to claim 1, wherein the alkylation agent is an alkylmagnesium halide compound.

14. A process according to claim 1, wherein the tin tetrahalide is added in step (b) such that the exotherm produced does not exceed 135° C.

15. A process according to claim 1, wherein all of the dialkyltin dihalide in step (d) is recycled to the contacting step (a).

16. A process for producing monobutyltin trichloride comprising:
   a. contacting dibutyltin dichloride with an alkylation agent and, optionally, tin tetrachloride, to form a tetrabutyltin mixture comprising tetrabutyltin, tributyltin chloride, and dibutyltin dichloride;
   b. reacting the tetrabutyltin mixture with tin tetrachloride to form a monobutyltin trichloride mixture comprising monobutyltin trichloride, dibutyltin dichloride and optionally tributyltin chloride;

c. processing the monobutyltin trichloride mixture to separately recover the monobutyltin trichloride and a dibutyltin dichloride stream comprising the dibutyltin dichloride and optionally tributyltin chloride; and d. recycling at least a portion of the dibutyltin dichloride stream recovered in step (c) to the contacting step (a).

17. A process according to claim 16, wherein the dibutyltin dichloride recovered in step (c) contains less than 5 mole % tributyltin chloride.

18. A process according to claim 16, wherein the dibutyltin dichloride recovered in step (c) contains less than 1 mole % tributyltin chloride.

19. A process for producing monooctyltin trichloride comprising:

a. contacting dioctyltin dichloride with an alkylation agent and, optionally, tin tetrachloride, to form a tetraoctyltin mixture comprising tetraoctyltin, trioctyltin chloride, and dioctyltin dichloride;

b. reacting the tetraoctyltin mixture with tin tetrachloride to form a monooctyltin trichloride mixture comprising monooctyl tin trichloride, dioctyltin dichloride and optionally trioctyltin chloride;

c. processing the monooctyltin trichloride mixture to separately recover the monooctyltin trichloride and a dioctyltin dichloride stream comprising the dioctyltin dichloride and optionally trioctyltin chloride; and d. recycling at least a portion of the dioctyltin dichloride stream recovered in step (c) to the contact step (a).

20. A process according to claim 19, wherein the dioctyltin dichloride recovered in step (c) contains less than 1 mole % trioctyltin chloride.

* * * * *